United States Patent [19]

Ezzell et al.

[11] Patent Number: 4,554,112
[45] Date of Patent: Nov. 19, 1985

[54] METHOD FOR THE PREPARATION OF VINYL COMPOUNDS

[75] Inventors: Bobby R. Ezzell, Lake Jackson; William P. Carl, Angleton; William A. Mod, Lake Jackson, all of Tex.

[73] Assignee: The Dow Chemical Company, Midland, Mich.

[21] Appl. No.: 259,137

[22] Filed: Apr. 30, 1981

Related U.S. Application Data

[63] Continuation-in-part of Ser. No. 197,420, Oct. 16, 1980, abandoned.

[51] Int. Cl.$^4$ ............................................ C07C 143/70
[52] U.S. Cl. .................................. 260/543 F; 568/56; 568/663; 568/684
[58] Field of Search ............... 260/543 F; 568/674, 568/677, 683, 684, 685, 615, 649, 655, 56, 656, 663

[56] References Cited

U.S. PATENT DOCUMENTS

| | | | |
|---|---|---|---|
| 3,282,875 | 11/1966 | Connolly et al. | 260/29.6 |
| 3,450,684 | 6/1969 | Darby | 260/87.5 |
| 4,153,804 | 4/1979 | Yamabe et al. | 560/183 |
| 4,209,635 | 6/1980 | Munekata et al. | 560/183 |

OTHER PUBLICATIONS

Daniel J. Vaughan, Nafion—An Electrochemical Traffic Controller, Du Pont Innovation, 4(3), 10–13, (1973).

Primary Examiner—Nicky Chan
Attorney, Agent, or Firm—J. H. Dickerson

[57] ABSTRACT

Fluorovinyl compounds having the formula

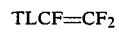

$$TLCF=CF_2$$

are prepared by reacting compounds having the formula

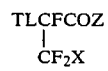

$$TLCFCOZ$$
$$|$$
$$CF_2X$$

for a time and at a temperature sufficient to form the vinyl compound:

where
X=Cl, Br or I;
Z=F, Cl, Br, OH, NRR', OA, or SA;
R and R' are independently selected from the group consisting of hydrogen, an alkyl having one or more than one carbon atom, and aryl;
A=Alkali metal, alkali earth metal, quaternary nitrogen, or R;
L=oxygen or sulfur; and
T=an alkyl or aryl radical which does not interfere with the reaction.

9 Claims, No Drawings

METHOD FOR THE PREPARATION OF VINYL COMPOUNDS

This is a continuation-in-part application of our co-pending application Ser. No. 197,420, filed Oct. 16, 1980, now abandoned.

The present invention relates to a method of producing vinyl compounds.

BACKGROUND OF THE INVENTION

U.S. Pat. No. 3,282,875 teaches pyrolyzing compounds having the general formulas

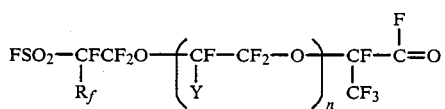

and

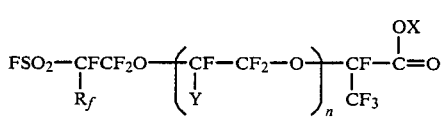

to form compounds represented by the general formula

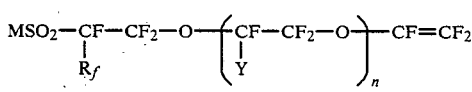

where
$R_f$ is F or a perfluoroalkyl radical having from 1–10 carbon atoms;
Y is F or a trifluoromethyl radical;
n is an integer of 1–3, inclusive;
M is F, hydroxyl radical, amino radical or OMe;
Me is an alkali metal or quaternary nitrogen radical; and
X is alkali metal.

Yields in the decarboxylation reaction of about 80 percent were obtained at high temperatures (about 300° C.) while yields of 20–30 percent were obtained at lower temperatures (about 200° C.). Also taught is the homo and copolymerization of the vinylether monomers to form useful polymers.

Fearn et al., *Journal of Polymer Science*, Volume 4, pp. 131–140, "Polymers and Terpolymers of Perfluoro-1,4-pentadiene" discloses that in the pyrolysis of sodium salts of carboxylic acids which contain fluorine and chlorine in the β position, sodium chloride is preferentially, but not exclusively eliminated. For example

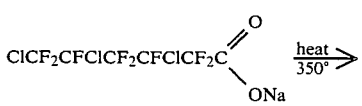

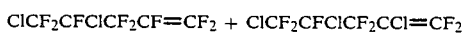

German Pat. No. 1,238,458 teaches that useful polymers are made from compounds of the general structure

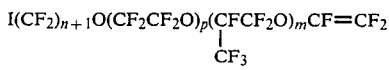

where n=1–8, p=0–5 and m=0–5. Crosslinked halogenated olefin copolymers are produced making use of the iodine group as a reactive site.

U.S. Pat. No. 3,450,684 to Darby teaches reacting a fluorocarbon ether with hexafluoropropylene epoxide, followed by decarboxylation; as shown by the following illustrated reactions:

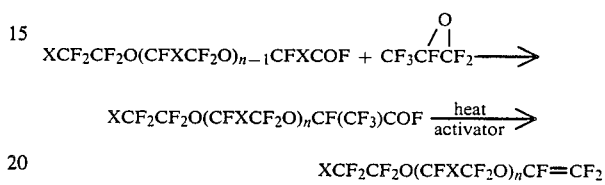

where X is F, Cl, H, $CF_2H$, $CF_2Cl$ or $CF_3$; n is at least 1.

U.S. Pat. No. 3,560,568 teaches the following reaction:

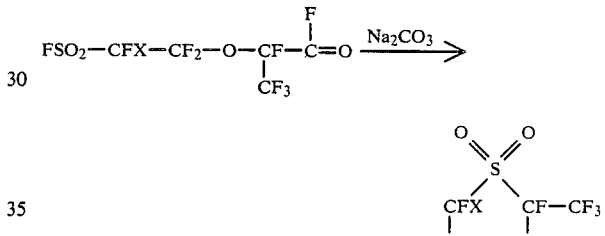

where X=F or $CF_3$.

R. D. Chambers, in his book *Fluorine in Organic Chemistry*, published by John Wiley & Sons, 1973, pages 211–212, teaches that carboxylic acid derivatives may be converted to olefins. The conversion involves the loss of carbon dioxide and formation of an intermediate carbon ion. The intermediate then loses NaF to form the resulting olefin.

BRIEF DESCRIPTION OF THE INVENTION

Fluorovinyl compounds having the formula

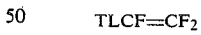

are prepared by reacting compounds having the formula

for a time and at a temperature sufficient to form the vinyl compound:
where
X=Cl, Br or I;
Z=F, Cl, Br, OH, NRR′, OA, or SA;
R and R′ are independently selected from the group consisting of hydrogen, an alkyl having one or more than one carbon atom, and aryl;
A=Alkali metal, alkali earth metal, quaternary nitrogen, or R;

L=oxygen or sulfur; and
T=an alkyl or aryl radical which does not interfere with the reaction.

DETAILED DESCRIPTION OF THE INVENTION

Fluorovinyl compounds having the formula $$TLCF=CF_2$$

are prepared by reacting one or more compounds of the formula $$\begin{array}{c} TLCFCOZ \\ | \\ CF_2X \end{array}$$

where
X=Cl, Br or I;
Z=F, Cl, Br, OH, NRR', OA or SA;
R and R' are independently selected from the group consisting of hydrogen, an alkyl having one or more than one carbon atom, and aryl;
A=Alkali metal, alkali earth metal, quaternary nitrogen, or R;
L=oxygen or sulfur; and
T=an alkyl or aryl radical which does not interfere with the reaction.

The present reaction method is a decarboxylation reaction conducted according to known methods, such as those taught by Chambers. The decarboxylation temperatures may be from about −50° C. to about 600° C. The decarboxylation reaction may be conducted in the presence of an activator to initiate and speed the reaction. The activator may be a base such as sodium carbonate or ZnO, silica or other known activators. It is particularly convenient to use $Na_2CO_3$ as the activator for the present decarboxylation reactions particularly where Z=F.

Optionally, a dispersant may be used to enhance the decarboxylation reactions. Suitable dispersants should be unreactive with the reactants and the products and may include such things as tetraglyme, diglyme or glyme.

The unexpected results obtained by the present invention and the mechanism by which the reactions occur are not fully understood. However, it is thought that the results are caused by X being Cl, Br or I, instead of F as is taught in the prior art.

The present preparation method is relatively independent from T. In other words, if the terminal group $$\begin{array}{c} LCFCOZ \\ | \\ CF_2X \end{array}$$

is present, the preparation method works. However, for the sake of complete disclosure, examples of complete molecules will be shown and discussed. However, the discussion and the specific illustrations do not limit the type of compounds which may be reacted or prepared. Thus, T may be any alkyl or aryl radical which does not interfere with the reaction. T may be branched or linear, substituted or unsubstituted alkyl having one or more carbon atoms or an aryl. T may contain oxygen in its structure. Preferably, T contains from 1 to about 20 carbon atoms.

In the present invention, L may be oxygen or sulfur. Preferably, L is oxygen. T, taken together with L, represents a nucleophile.

The general chemistry employed for preparing the intermediates or starting materials for the present invention is well known. Fluorocarbon epoxides are known to react with nucleophiles to form acid fluoride intermediates. The starting materials employed to prepare the fluorovinyl compounds of the present invention are conveniently prepared by reaction of 3-chloro or bromopentafluoropropylene oxide with a nucleophile:

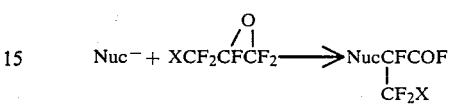

X=Cl, Br or I,
Nuc=a nucleophile.

These acid fluoride intermediates may then be converted to other acid derivatives by well known reactions of acid fluorides with bases, water, alcohols, thiols, ammonia or amines, if desired, before decarboxylation. The acids themselves (Z=OH) are easily converted to acid chlorides or bromides by reaction with halogenating agents such as $PCl_5$ or $PBr_5$.

This type chemistry is discussed in Chambers (pp. 230–232) and more extensively in P. Tarrant et al., *Fluorine Chem. Revs.*, 5, pp. 85–93 (1971). In general, the chemistry taught for reactions of hexafluoropropylene oxide (X=F above) has been found to apply equally well to halogen (Cl, Br or I) substituted fluoropropylene oxides used to prepare the intermediates used in the present invention. Nucleophiles such as alcohols, thiols, alkoxides, thioalkoxides, phenols or phenoxides react readily with the center carbon of the epoxide to form an intermediate fluoroalkoxide which can then either lose fluoride to form an acid fluoride or react with additional epoxides which are subsequently terminated by loss of fluoride.

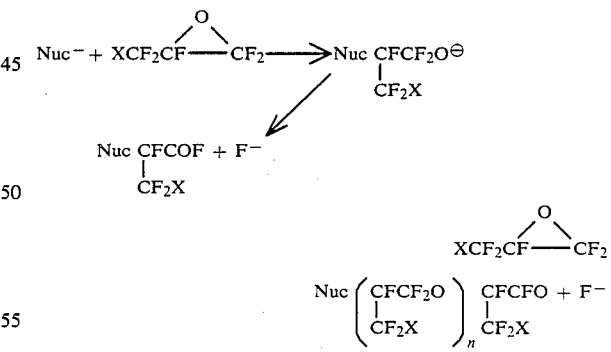

Decarboxylation reactions performed directly on the acid fluoride terminal group or derivatives have been shown to be relatively independent of the rest of the molecule and to offer an improvement over the common method of preparing fluorocarbon olefins by reacting nucleophiles with hexafluoropropylene oxide and then decarboxylating.

Conversion yields as high as 99+% are obtained with temperatures as low as 65°–70° C. However, excellent yields may be obtained using temperatures from about −50° C. to about 200° C.

The following examples illustrate the invention but in no way limit the scope of the invention to the compounds shown in the examples.

EXAMPLE 1

300 Ml of dry tetraglyme and 62.2 grams anhydrous $Na_2CO_3$ were added to a 1000 ml 3-neck flask equipped with a magnetic stirrer, thermometer, reflux condenser and an inlet port. Two $-78°$ C. cold traps were located in series downstream of the reflux condenser. 154 Grams of product containing 92.1 percent

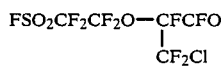

as identified by GCMS and VPC analyses were added dropwise. There was a slight temperature rise from 22° C. to about 35° C. over the period during the addition. Temperature of reactor was increased to 82° C. At this temperature there was obtained considerable reflux. The reflux condenser was removed and the product collected in the cold traps. The temperature was raised to 150° C. with the system under vacuum. 80.5 Grams of the product were collected in the first cold trap and 1 gm in the second. The product was analyzed by VPC and IR. Essentially, all of the starting material had reacted. The yield was 70.6 percent as a product analyzing 95 percent $FSO_2CF_2CF_2OCF=CF_2$ by VPC. IR analysis showed bands as follows:

| Vinyl Ether | 1830 wave no. |
| --- | --- |
| $-SO_2F$ | 1460 wave no. |
| $-SO_2F$ | 1240 wave no. |
| $-SF$ | 810 wave no. |
| B.Pt. | 75°–76° C. |

A direct titration of the unsaturation in the above product with $Br_2$ in $CCl_4$ was done to further confirm the structure. Twenty milliliters of $CCl_4$ solution containing 2 g $Br_2$ were made up as titrant. Two grams of the monomer were dissolved into 5 ml $CCl_4$ and titrated at ambient temperature to the point of color persistence. The titration required 10.9 ml of the bromine solution of 0.0068 mole of bromine. The apparent molecular weight of the monomer is then 2 g/0.0068 mole = 293.6 or a difference from the proposed structure of $(293.6-280)/280 \times 100 = 5.4\%$. This value is in excellent agreement with the purity indicated by VPC analysis.

COMPARATIVE EXAMPLE 1

100 Ml of tetraglyme and 9.84 gms anhydrous $Na_2CO_3$ were added to a 500 ml 3-neck flask equipped with a magnetic stirrer, thermometer, $-78°$ C. reflux condenser, and a dropping funnel. Two $-78°$ C. cold traps were located in series downstream of the reflux condenser. 29.35 Grams of product analyzing 84.4 percent

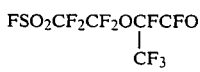

by VPC were added dropwise over a 3-hour period with evolution of $CO_2$. The reflux condenser was removed. The reactor was heated to 78°–80° C. while maintaining a slight $N_2$ sweep through the reactor to remove the product. 15.69 Grams were recovered in the first cold trap and 0.6 gram in the second. The product was analyzed by VPC and IR. Conversion of the

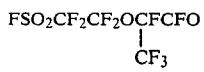

was essentially complete giving a yield of 77 percent to a product which was not a fluorosulfonylperfluoro vinyl ether. Following is the IR analysis:

| Wave No. | |
| --- | --- |
| 1360 | O<br>—S—<br>O |
| 1150 | O<br>—S—<br>O |
| B. Pt. ~80° C. | |

Product was believed to be the sulfone.

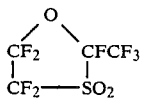

Described in U.S. Pat. No. 3,560,568.

EXAMPLE 2

17 Grams of a mixture containing 68 percent

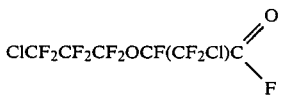

and higher homologs as analyzed by GC-mass spectroscopy were added dropwise to a stirred 3-neck reaction vessel containing 50 ml dried tetraglyme and 7.1 grams dried $Na_2CO_3$ and fitted with a thermometer, heating mantle, and a stillhead with vacuum takeoff and double dry ice acetone trap under inert purge. Gas evolution was observed and a temperature rise from 25° C. up to 33° C. was observed during addition. After continued stirring for 1 hour, a 5 mm vacuum was applied and the temperature was raised slowly up to 100° C. in the vessel. Seven grams of material were collected in the primary collection receiver and identified as 97.1% $ClCF_2CF_2CF_2OCF=CF_2$. Raising the temperature under vacuum, up to 145° C., resulted in collection of an additional 2 grams material which was analyzed by GC-mass spectroscopy and I.R. as 22.35% $ClCF_2CF_2CF_2OCF=CF_2$ representing an 81% yield of $ClCF_2CF_2CF_2OCF=CF_2$. VPC analysis of the solvent in the reaction vessel showed some $ClCF_2CF_2CF_2OCF=CF_2$ remaining along with higher homologs.

COMPARATIVE EXAMPLE 2

A mixture (35 gms) containing 31.7 percent of

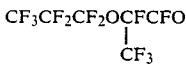

plus higher homologs was added to a mixture of 15.5 gms $Na_2CO_3$ in 50 ml of tetraglyme at room temperature. After several hours and cessation of $CO_2$ evolution, the mixture was raised to 120° C. whereupon there were indications of some slow $CO_2$ evolution. After several hours at this condition, pulling a vacuum on the system to remove product resulted in little or no evidence, by VPC and I.R., of vinyl ether formation. The temperature of the reactor was then raised to 160°–170° C. under atmospheric pressure. Under these conditions, boiling of the mixture resulted. The product collected (8 gms) showed a VPC peak at 0.74 min. retention time and absorption in the I.R. at 1840 cm$^{-1}$ indicating formation of the vinyl ether.

EXAMPLE 3

15 Ml of tetraglyme and 1.0 gm of anhydrous $Na_2CO_3$ were added to a 3-neck flask equipped with a thermometer, stirrer and reflux condenser. Cold traps (−78° C.) were downstream of the condenser and a slight back pressure of $N_2$ was maintained by means of a bubbler $FSO_2CF_2CF_2OCF(CF_3)CF_2OCF(CF_2Cl)$-CFO (3 gms) were added and after a brief evolution of $CO_2$, the temperature was raised to 80° C. and held there for several hours until $CO_2$ evolution ceased. A vacuum was pulled on the reactor and the temperature was slowly increased to 136° C. while collecting 1.5 gms of product in the cold trap. The majority of the product was collected before the temperature reached 90° C. VPC analysis showed additional product remaining in the tetraglyme solvent. The product was confirmed as

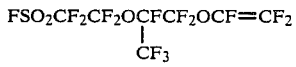

by mass spectroscopy, I.R. and $F^{19}$ NMR.

EXAMPLE 4

To a 100 ml 3-neck flask were added 50 ml of dry tetraglyme and 9.75 gms of anhydrous $Na_2CO_3$. The flask was equipped with a stirring bar, reflux condenser, thermometer, and inlet port. Two −78° C. cold traps in series were located downstream of the reflux condenser. A slight back pressure was maintained on the system with a dry $N_2$ bubbler. 15.95 Grams of

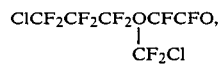

were added slowly at room temperature. There was a small temperature rise to about 35° C., and an evolution of $CO_2$, upon addition of the acid fluoride. The temperature was increased to 67°–68° C. and held there for 2.5 hours. The product was then distilled from the reactor. 12.59 Grams of product were collected which analyzed 97.37 percent as $ClCF_2CF_2CF_2OCF=CF_2$. This represents a 99.3 percent yield to the vinyl ether.

What is claimed is:

1. A method of preparing a compound having the formula:

comprising:
reacting a compound having the general formula:

for a time and at a temperature sufficient to convert at least a portion of compound (II) directly into compound (I);
where
X = Cl, Br or I;
Z = F, Cl, Br, OH, NRR', OA, or SA;
R and R' are independently selected from the group consisting of hydrogen, an alkyl having one or more than one carbon atom, and aryl;
A = alkali metal, alkali earth metal, quaternary nitrogen, or R;
L = oxygen, or sulfur; and
T = an alkyl or aryl radical which does not interfere with the reaction.

2. The method of claim 1 carried out in the presence of an activator.

3. The method of claim 2 where the activator is a base.

4. The method of claim 1 where the temperature is from about −50° C. to about 200° C.

5. The method of claim 1 where L is oxygen.

6. The method of claim 1 where T is an alkyl having from 1 to 20 carbon atoms.

7. The method of claim 6 where T is a perhalogenated radical.

8. The method of claim 6 where T contains oxygen in its structure.

9. The method of claims 1, 2, 3, 4, 5, 6, 7 or 8 where X is Cl.

* * * * *